(12) United States Patent
Hong

(10) Patent No.: US 8,419,425 B2
(45) Date of Patent: Apr. 16, 2013

(54) DENTAL MODEL ARTICULATOR

(75) Inventor: Chang Sik Hong, Daegu (KR)

(73) Assignee: Bowon Dental Co., Ltd., Daegu (KR)

( * ) Notice: Subject to any disclaimer, the term of this patent is extended or adjusted under 35 U.S.C. 154(b) by 0 days.

(21) Appl. No.: 13/254,142

(22) PCT Filed: Nov. 25, 2009

(86) PCT No.: PCT/KR2009/006975
§ 371 (c)(1),
(2), (4) Date: Dec. 13, 2011

(87) PCT Pub. No.: WO2010/104261
PCT Pub. Date: Sep. 16, 2010

(65) Prior Publication Data
US 2012/0082957 A1     Apr. 5, 2012

(30) Foreign Application Priority Data
Mar. 11, 2009  (KR) .......................... 10-2009-0020833

(51) Int. Cl.
*A61C 11/00*  (2006.01)
(52) U.S. Cl.
USPC ............................................. 433/58; 433/60
(58) Field of Classification Search .................... 433/54, 433/57, 58, 60
See application file for complete search history.

(56) References Cited

U.S. PATENT DOCUMENTS

| | | | |
|---|---|---|---|
| 566,949 A * | 9/1896 | Walker | 433/58 |
| 912,748 A * | 2/1909 | Snow | 433/58 |
| 981,430 A * | 1/1911 | Kennedy | 433/60 |
| 4,045,873 A * | 9/1977 | Burnett | 433/58 |
| 4,496,320 A * | 1/1985 | Hwang et al. | 433/60 |
| 5,842,857 A | 12/1998 | Andrews | |
| 6,394,804 B1 * | 5/2002 | Pacino et al. | 433/64 |
| 6,780,011 B2 * | 8/2004 | Davidov et al. | 433/64 |
| 2004/0043354 A1 * | 3/2004 | Chou | 433/60 |

FOREIGN PATENT DOCUMENTS

KR    20-0220278 Y1    4/2001
KR    10-2006-0074406 A    7/2006

* cited by examiner

*Primary Examiner* — Ralph Lewis
(74) *Attorney, Agent, or Firm* — Mitchell P. Brook; McKenna Long & Aldridge LLP

(57) ABSTRACT

Disclosed is a dental model articulator configured to combine maxillary and mandibular dental model casts with each other. The dental model articulator includes a frame, an arm member rotatably and reciprocatively supported to the frame, an elastic bias unit frontward elastically pressing the arm member with respect to the frame, a first connecting unit formed in the arm member to be connected with the maxillary dental model cast, and a second connecting unit connected to the frame to move reciprocatively through at least one penetration hole and combined with the mandibular dental model cast.

3 Claims, 4 Drawing Sheets

DENTAL MODEL ARTICULATOR

TECHNICAL FIELD

The present invention relates to a dental model articulator, and more particularly, to a disposable dental model articulator having good capability of positioning and retaining maxillary and mandibular dental model casts.

BACKGROUND ART

Food is chewed by teeth such that upper and lower teeth are aligned through movement of jaw joints.

If teeth are damaged, misalignment may be caused, resulting in dental dysfunction. In this case, in order to cure the damaged teeth, prosthetic appliance may be used. In fabricating the prosthetic appliance, an articulator is used to check a teeth alignment state.

A dental model articulator is a device to assist to process prosthetic appliance to allow the prosthetic appliance to be compatible with existing teeth by mounting dental models and simulating jaw joint movement.

There are numerous types of articulators ranging from very simple openable type devices to highly sophisticated and mechanically complex devices. In general, based on the adjustability factor, articulators fall into the following categories: nonadjustable articulators, semiadjustable articulators, and fully adjustable articulators.

The nonadjustable articulator includes a hinge type articulator and an average movement articulator. The hinge type articulator is a simplest type articulator that is not structurally adjustable but is capable of moving only up and down in open and closed positions or lateral movement in a limited range.

Since the average movement articulator having a condylar guidance angle of 30° on the average is fixed, it is not possible to adjust individuals having different condylar guidance angles. When tooth models are attached to the average movement articulator, only the occlusal record at the centric position between upper and lower jaws is necessary, there is no way of adjusting a condylar path. However, since the average movement articulator is capable of moving maxillary member, it has the advantage of lateral movement.

The semiadjustable articulator is capable of adjusting condylar paths and is adjustable by a centric occlusal record, anterior occlusal record and a lateral occlusal record, thereby producing an improved denture or restorative material, compared to a case where the nonadjustable articulator.

The fully adjustable articulator is most sophisticated but is mechanically complex, requiring much more complicated preparation and manipulation works than the semiadjustable articulator. Thus, it is quite difficult to commercialize the fully adjustable articulator.

Meanwhile, in a dental technologist's office or laboratory, the articulators are suitably utilized based on their characteristics. The nonadjustable articulator, specifically, the hinge type articulator is hardly used. The average movement articulator is typically used in temporary dentures, mechanically simple crowns or bridges, and so on. The semiadjustable articulator having a wide variety of dental applications are suitably used with fabrication of complete dentures or partial dentures.

Among the articulators, an average movement articulator is disclosed in Korean Utility Model Registration No. 0220295. The disclosed articulator is configured such that a maxillary dental model cast is fixedly combined with an upper model fixing unit using plaster, etc. and a mandibular dental model cast is then combined with a lower model fixing unit using plaster, etc. However, since the conventional articulator uses plaster, quite a long time is required to harden the plaster. In addition, once the casts are fixedly combined, it is not easy to separate the casts.

In particular, it is necessary to accurately align and fix occlusal positions of the maxillary dental model cast and mandibular dental model cast. However, in a case where the occlusal positions are misaligned, the misalignment cannot be corrected.

DISCLOSURE OF THE INVENTION

In order to overcome the above-mentioned shortcomings, the present invention provides a dental model articulator which can easily correct occlusal positions while easily fixing and separating dental models.

According to an aspect of the invention, there is provided a dental model articulator configured to combine a maxillary dental model cast and a mandibular dental model cast, the dental model articulator including a frame, an arm member rotatably and reciprocatively supported to the frame, an elastic bias unit frontward elastically pressing the arm member with respect to the frame, a first connecting unit formed in the arm member to be connected with the maxillary dental model cast, and a second connecting unit connected to the frame to move reciprocatvely through at least one penetration hole and combined with the mandibular dental model cast.

The frame, the arm member, the first connecting unit and the second connecting unit may be made of synthetic materials.

In addition, the frame may include first and second support parts extending upward from a base part having the penetration hole to be spaced apart from each other, third support parts retreating rearward from top ends of the first and second support parts to be integrally connected to each other, and first and second locking parts extending upward from the top ends of the first and second support parts to rear positions and forming an accommodation groove having an open posterior part to allow the arm member to be inserted into the accommodation groove.

The first connecting unit may include a connection guide unit integrally formed with a central part of the arm member and having a spherical connecting pin protruding frontward, and a main connecting unit having a first body part, a first insertion unit having a hemispherical accommodation groove formed in a rear surface of the first body part and detachably formed with respect to the spherical connecting pin by an interference fit manner, and a first connecting protrusion ledge protruding on a front surface of the first body part so as to be inserted into and connected to the maxillary dental model cast, and the second connecting unit may include a second body part, cylindrical rods configured to advance and retreat along the penetration hole formed in a rear surface of the second body part of the frame, and a second connecting protrusion ledge protruding on a front surface of the second body part so as to be inserted into and connected to the mandibular dental model cast.

According to the dental model articulator of the present invention, the dental model cast can be engaged with a frame using a detachable connecting device, and a fixing position of the mandibular dental model cast can be adjustably fixed using reciprocating a rod, thereby facilitating fixed alignment of occlusal positions and easily correcting misalignment by separating the dental model casts detachably engaged with the frame.

BRIEF DESCRIPTION OF THE DRAWINGS

The objects, features and advantages of the present invention will be more apparent from the following detailed description in conjunction with the accompanying drawings, in which.

BEST MODE FOR CARRYING OUT THE INVENTION

Hereinafter, a dental model articulator according to the preferred embodiments of the present invention will be explained in detail referring to the accompanying drawing.

Figure 1:
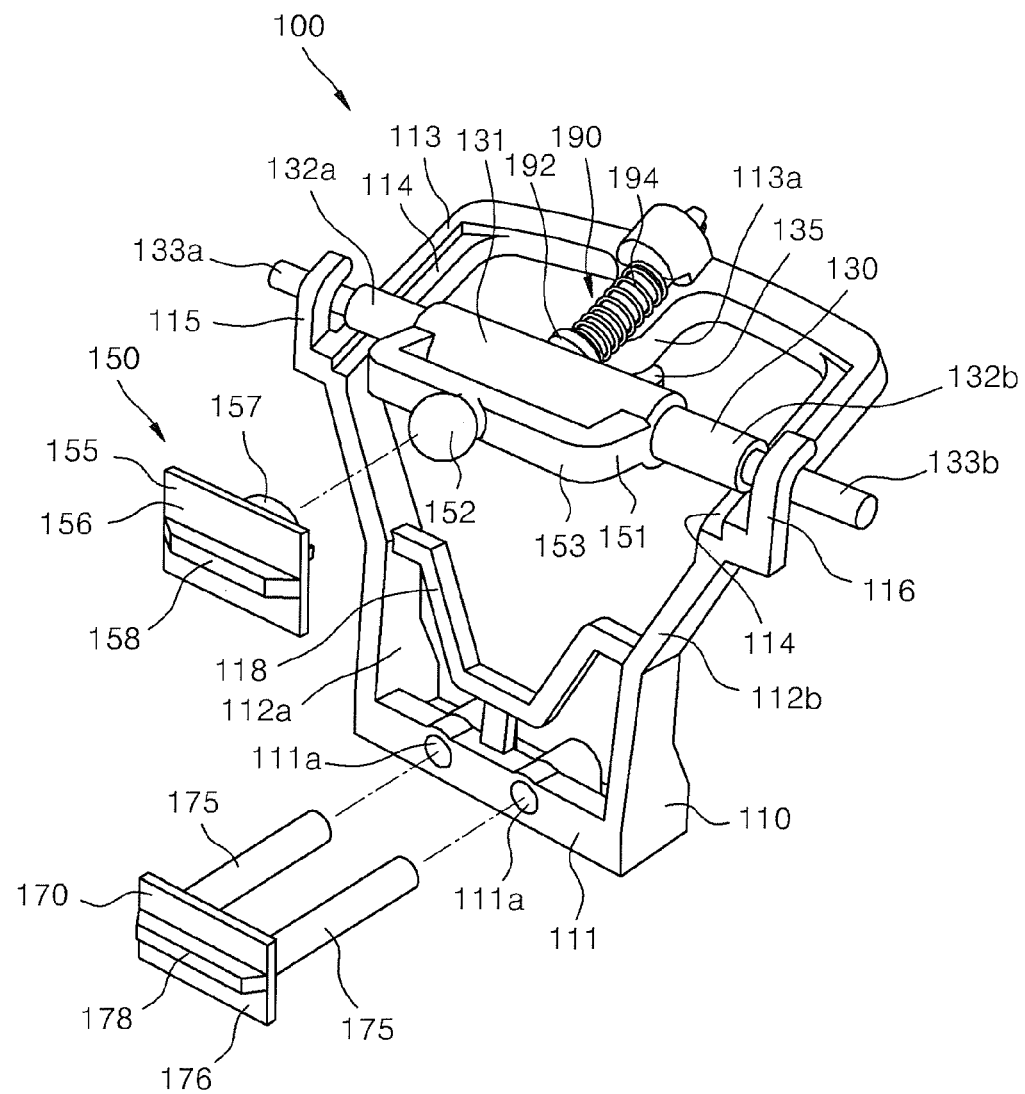
FIG. 1 is a perspective view showing a dental model articulator according to an embodiment of the present invention.
Figure 2:
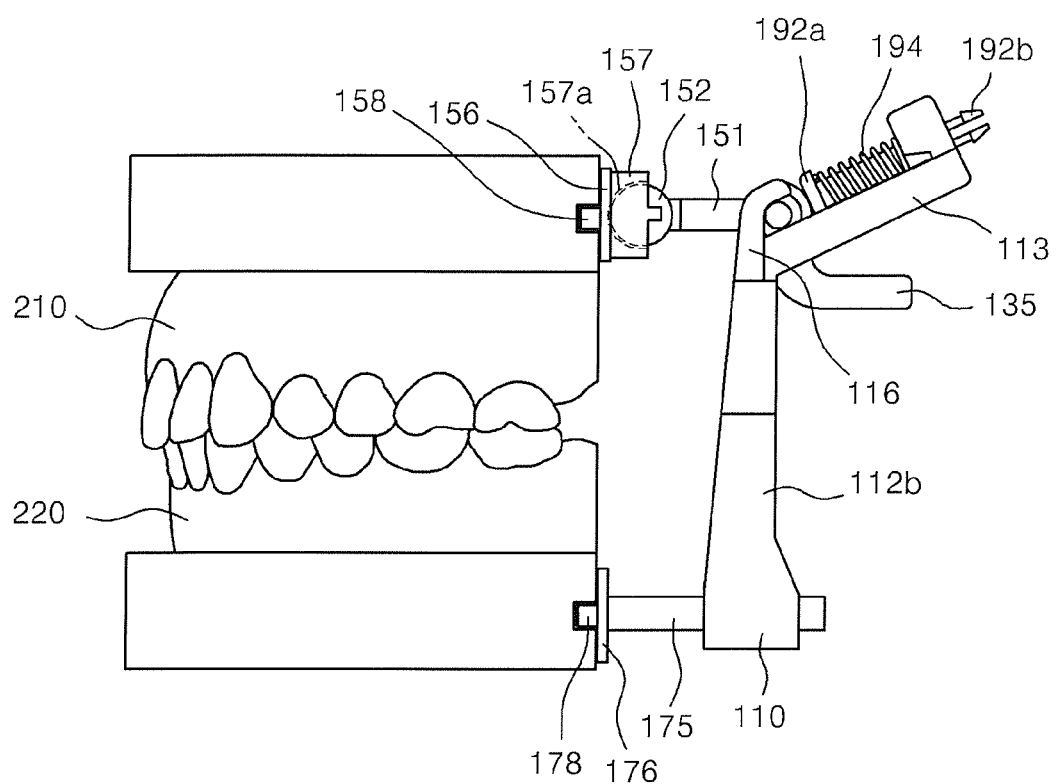
FIG. 2 is a side view illustrating a state in which a dental model caster is engaged with the dental model articulator shown in FIG. 1.

FIG. 1 is a perspective view showing a dental model articulator according to an embodiment of the present invention, and FIG. 2 is a side view illustrating a state in which a dental model caster is engaged with the dental model articulator shown in FIG. 1.

Referring to FIGS. 1 and 2, the articulator 100 includes a frame 110, an arm member 130, a first connecting unit 150, a second connecting unit 170 and an elastic bias unit 190.

The frame 110 is formed to support the arm member 130 to be described later, and is configured such that the second connecting unit 170 can be inserted to be reciprocatively supported.

The frame 110 is preferably integrally formed from a synthetic resin, e.g., a plastic material. For convenience of explanation, the frame 110 is divided into a base part 111, first to third support parts 112a, 112b and 113, and first and second locking parts 115 and 116.

The base part 111 is a part having a planar bottom surface so as to be supported by a support target body and extending a predetermined length in left and right directions and has penetration holes 111a spaced apart from each other to allow rods 175 of the second connecting unit 170, which will later be described. The penetration holes 111a are shaped of hollow cylinders so as to penetrate back and forth into the base part 111.

The first and second support parts 112a and 112b extend upward from opposite sides of the base part 111 to be symmetrical with each other. The first and second support parts 112a and 112b extend to be inclined at a predetermined height so as to be away from each other.

Reference numeral 118 refers to a reinforcement part for lateral strength of the first and second support parts 112a and 112b by connecting the first and second support parts 112a and 112b with the base part 111. If the frame 110 has a small size, the reinforcement part may not be provided.

The third support part 113 has a part extending in a 'U' shape, forming a closed loop together with the first and second support parts 112a and 112b in such a manner that the third support part 113 rearward extends from top ends of the first and second support parts 112a and 112b to be integrated into the first and second support parts 112a and 112b.

The part of the third support part 113 rearward extending from the top ends of the first and second support parts 112a and 112b has binding guide ledges 114 having a stepped portion to prevent the third support part 113 from being separated in the left and right directions, while guiding rearward retreat of the arm member 130, which will later be described.

The first and second locking parts 115 and 116 are configured such that they upward extend from the top ends of the first and second support parts 112a and 112b and then rearward extend, forming an accommodation groove having an open posterior part, into which the arm member 130 may be inserted.

An insertion hole, into which a compressive pin 192 of the elastic bias unit 190 may be inserted, is formed at the center of the third support part 113.

In addition, an auxiliary guide part 113a extending to frontward protrude a predetermined length is formed at the center of the third support part 113, the auxiliary guide part 113a guiding the compressive pin 192 to advance and retreat.

The arm member 130 is configured to be inserted into an accommodation groove of each of the first and second locking parts 115 and 116 of the frame 110 so as to be rotated.

In detail, the arm member 130 has a central part 131 having a first outer diameter, first and second side parts 132a and 132b extending lengthwise from the central part 131 in opposite sides and each having a second outer diameter smaller than the first outer diameter, and third and fourth side parts 133a and 133b extending lengthwise from the first and second side parts 132a and 132b and each having an outer diameter smaller than the second outer diameter.

Lengths ranging from the central part 131 to the first and second side parts 132a and 132b may correspond to a distance between of the binding guide ledges 114 of the third support part 113.

A stopper 135 rearward extends a predetermined length from a bottom portion of the central part 131 and may advance or retreat to a predetermined lower portion of the auxiliary guide part 113a.

The stopper 135 functions to limit a rotation range of the first connecting unit 150 when the first connecting unit 150 connected to a front portion of the arm member 130 rotates downward.

The first connecting unit 150 is installed at the central part 131 of the arm member 130 to be connected with the maxillary dental model cast 210.

In detail, the first connecting unit 150 has a connection guide unit 151 having a spherical connecting pin 152, and a main connecting unit 155 detachably formed with respect to the spherical connecting pin 152 and combined with the maxillary dental model cast 210.

The connection guide unit 151 has the spherical connecting pin 152 formed at the center of the extending part 153 protruding on the central part 131 of the arm member 130 the spherical connecting pin 152 protruding frontward.

The main connecting unit 155 has a first body part 156, a first insertion unit 157 and a first connecting protrusion ledge 158.

The first body part 156 has a rectangular plate shape.

The first insertion unit 157 is formed on a rear surface of the first body part 156 and has a hemispherical accommodation groove 157a detachably formed with respect to the spherical connecting pin 152 by an interference fit manner.

The first connecting protrusion ledge 158 is formed at the center of a front surface of the first body part 156 so as to laterally protrude. The first connecting protrusion ledge 158 is formed to be inserted into an insertion groove formed in the maxillary dental model cast 210 to be used in connecting the maxillary dental model cast 210.

The elastic bias unit 190 is installed to frontward elastically press the arm member 130 with respect to the frame 110.

In detail, the elastic bias unit 190 has a compressive pin 192 and a spring 194.

The compressive pin 192 has a head 192a provided at an end contacting the arm member 130 to prevent the spring 194 from being dislodged. The head 192a has the other end having arrow-headed branches 192b spaced apart from each other to prevent the head 192a from being dislodged by shape restoration once it is inserted into an insertion hole while reducing the external size.

The second connecting unit 170 is combined with the frame 110 through the penetration holes 111a formed in the frame 110 so as to advance and retreat, and is formed to be used in connecting the mandibular dental model cast 220.

In detail, the second connecting unit 170 has a second body part 176, two rods 175 and a second connecting protrusion ledge 178.

The second body part 176 has a rectangular plate shape.

The spaced-apart two rods 175 are formed on a rear surface of the second body part 176 and extend a predetermined length in a cylindrical shape to as to advance and retreat along the penetration holes 111a formed in the frame 110.

If occlusal positions are determined by allowing the rods 175 to advance and retreat through the penetration holes 111a in a state in which the rods 175 are combined with the mandibular dental model cast 220 to be described later, the rods 175 are preferably formed to have a small distance from the penetration holes 111a so as to fix the penetration holes 111a formed in the frame 110 and the rods 175 by injecting an instant glue between the penetration holes 111a and the rods 175.

The second connecting protrusion ledge 178 protrudes on a front surface of the second body part 176 to be inserted into the mandibular dental model cast 220 and combined therewith.

Figure 3:
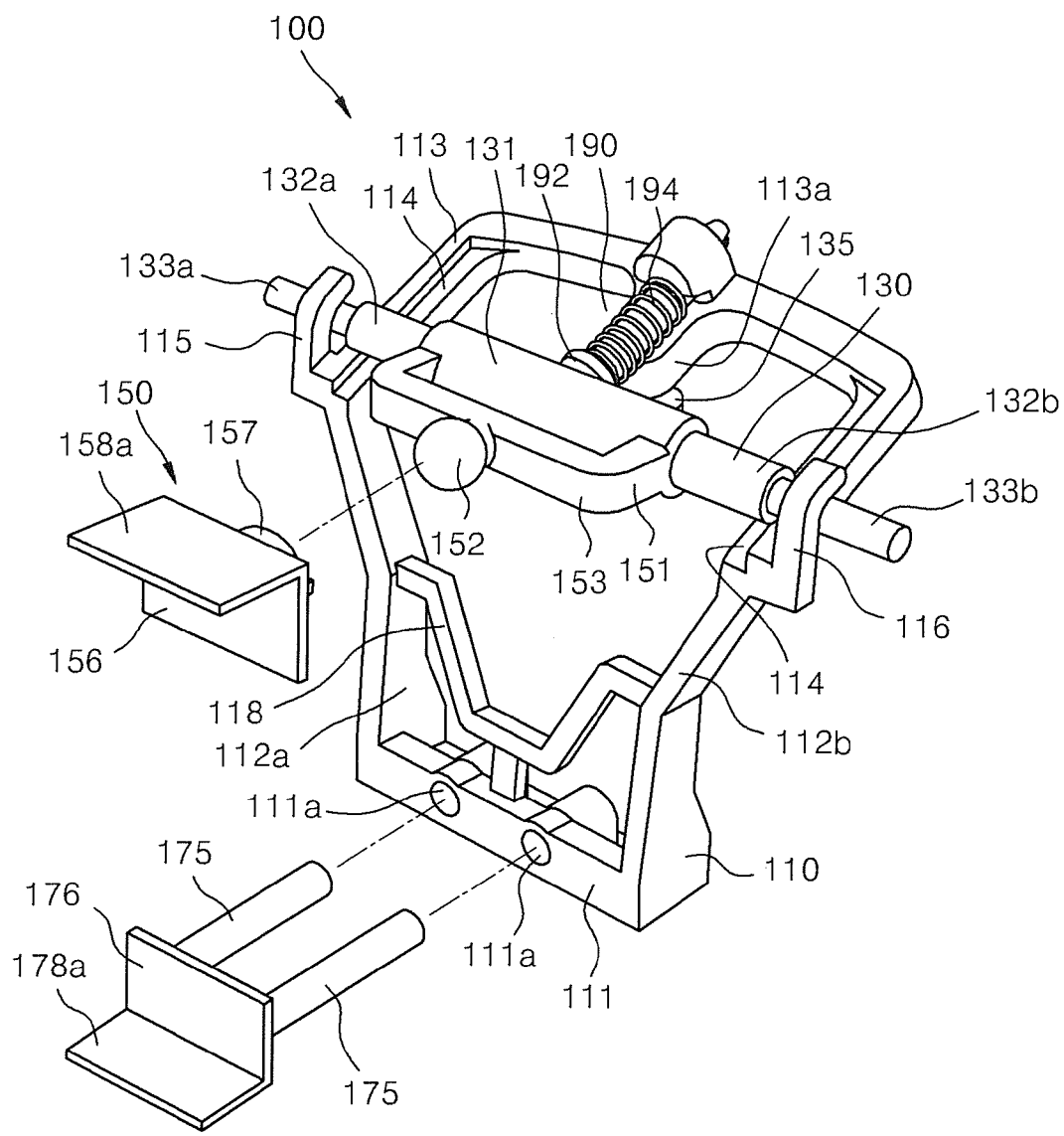
FIG. 3 is a perspective view showing a dental model articulator according to another embodiment of the present invention.
Figure 4:
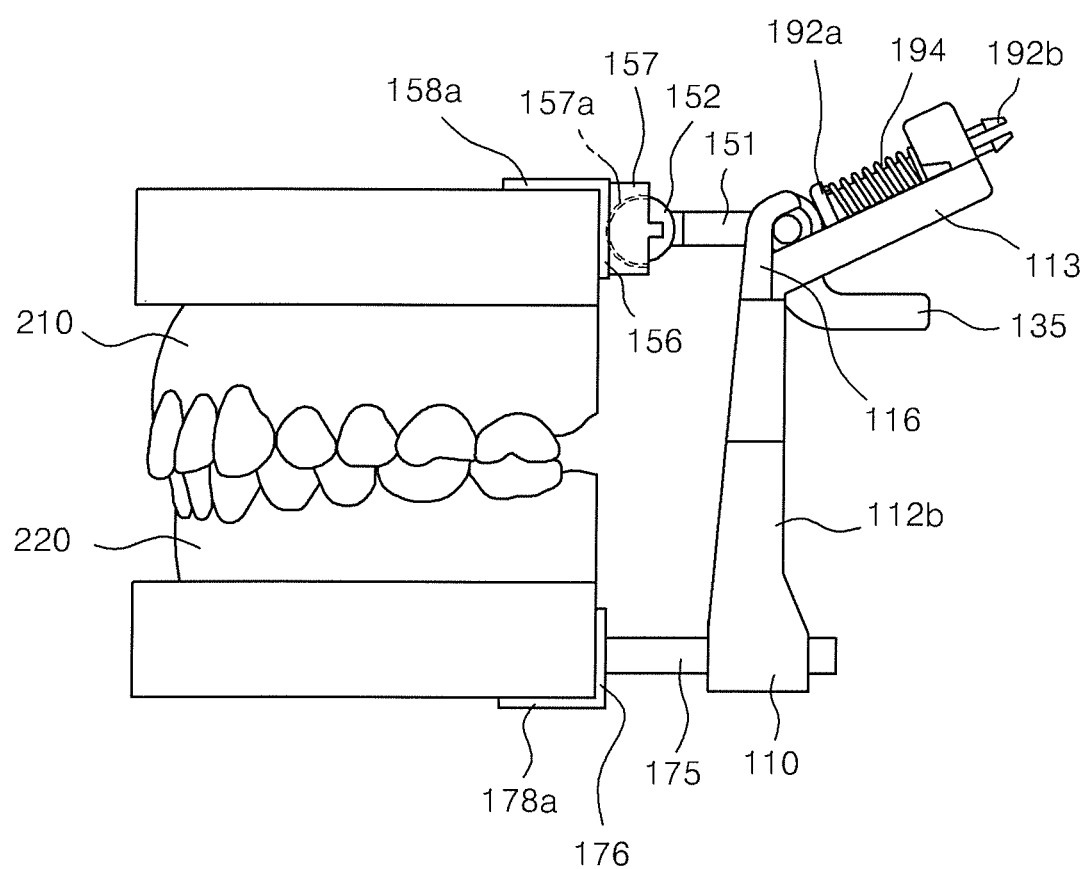
FIG. 4 is a side view illustrating a state in which a dental model caster is engaged with the dental model articulator shown in FIG. 3.

As shown in FIGS. 3 and 4, the first connecting protrusion ledge 158a of the first connecting unit 150 and the second connecting protrusion ledge 178a of the second connecting unit 170 may extend from top or bottom ends of the first or second body part 156 (or 176) to protrude frontward in an 'L' shape. In this case, the maxillary dental model cast 210 and the mandibular dental model cast 220 may be combined with each other using instant glue in a state in which they are brought into contact with each other so as to be surrounded from external sides without forming separate insertion grooves.

The frame 110, the arm member 130, the first connecting unit 150 and the second connecting unit 170 are preferably made of a synthetic resin material, e.g., a plastic material.

In the articulator 100 having the aforementioned configuration, the maxillary dental model cast 210 and the mandibular dental model cast 220 are first combined with each other using an adhesive, such as an instant glue, so as to allow the first connecting protrusion ledge 158a of the first connecting unit 150 and the second connecting protrusion ledge 178a of the second connecting unit 170 to be inserted into the maxillary dental model cast 210 and the mandibular dental model cast 220, respectively, and then combined with the frame 110 and the arm member 130. Here, if the occlusal position of the mandibular dental model cast 220 is adjusted and determined while advancing and retreating the rods 175, an adhesive, such as instant glue, is applied between the rods 175 and the penetration holes 111a for fixing the mandibular dental model cast 220.

In addition, the occlusal position of the maxillary dental model cast 220 may also be fixed by injecting instant glue into the spherical connecting pin 152.

Although exemplary embodiments of the present invention have been described in detail hereinabove, it should be understood that many variations and modifications of the basic inventive concept herein described, which may appear to those skilled in the art, will still fall within the spirit and scope of the exemplary embodiments of the present invention as defined by the appended claims.

What is claimed is:

1. A dental model articulator configured to combine a maxillary dental model cast and a mandibular dental model cast, the dental model articulator comprising:
   a frame including:
      first and second support parts extending upward from a base part having a penetration hole to be spaced apart from each other;
      a third support part retreating rearward from top ends of the first and second support parts to be integrally connected to each other, the third support part having binding guide ledges with a stepped portion; and
      first and second locking parts extending upward from the top ends of the first and second support parts to rear positions and forming an accommodation groove having an open posterior part;
   an arm member rotatably and reciprocatively supported to the frame, the arm member having a central part having a first outer diameter, first and second side parts extending lengthwise from the central part in opposite sides and each having a second outer diameter smaller than the first outer diameter, and third and fourth side parts extending lengthwise from the first and second side parts and each having an outer diameter smaller than the second outer diameter, lengths ranging from the central part to the first and second side parts corresponding to a distance between the binding guide ledges of the third support part, the open posterior part allowing the arm member to be inserted into the accommodation groove and the stepped portion preventing the arm member from being separated in the left and right directions, while guiding rearward retreat of the arm member;
   an elastic bias unit frontward elastically pressing the arm member with respect to the frame;
   a first connecting unit formed in the arm member to be connected with the maxillary dental model cast; and
   a second connecting unit connected to the frame to move reciprocatively through at least one penetration hole and combined with the mandibular dental model cast.

2. The dental model articulator of claim 1, wherein the frame, the arm member, the first connecting unit and the second connecting unit are made of synthetic materials.

3. The dental model articulator of claim 1, wherein the first connecting unit comprises:
   a connection guide unit integrally formed with a central part of the arm member and having a spherical connecting pin protruding frontward; and
   a main connecting unit having a first body part, a first insertion unit having a hemispherical accommodation groove formed in a rear surface of the first body part and detachably formed with respect to the spherical connecting pin by an interference fit manner, and a first connecting protrusion ledge protruding on a front surface of the first body part so as to be inserted into and connected to the maxillary dental model cast, and
   wherein the second connecting unit comprises:
   a second body part;

cylindrical rods configured to advance and retreat along the penetration hole formed in a rear surface of the second body part of the frame; and a second connecting protrusion ledge protruding on a front surface of the second body part so as to be inserted into and connected to the mandibular dental model cast.

\* \* \* \* \*